United States Patent [19]

Kowite et al.

[11] Patent Number: 4,840,660

[45] Date of Patent: Jun. 20, 1989

[54] PLANT GROWTH REGULATOR DISPERSIONS

[75] Inventors: William J. Kowite; Stephen L. Oestreicher, both of Raleigh, N.C.

[73] Assignee: Rhone Poulenc Nederlands B.V., Amstelveen, Netherlands

[21] Appl. No.: 122,626

[22] Filed: Nov. 19, 1987

Related U.S. Application Data

[63] Continuation of Ser. No. 814,898, Dec. 30, 1985, abandoned.

[51] Int. Cl.[4] .............................................. A01N 57/12
[52] U.S. Cl. .................................... 71/86; 71/DIG. 1
[58] Field of Search .............................. 71/86, DIG. 1

[56] References Cited

U.S. PATENT DOCUMENTS

| | | | |
|---|---|---|---|
| 3,399,991 | 9/1968 | Littler | 71/120 |
| 3,879,188 | 4/1975 | Fritz et al. | 71/86 |
| 3,960,540 | 6/1976 | Crosby | 71/86 |
| 3,997,595 | 12/1976 | Jung et al. | 71/86 |
| 4,144,064 | 3/1979 | Esposito | 71/86 |
| 4,218,444 | 8/1980 | Koundakjian | 514/120 |
| 4,240,819 | 12/1980 | Fritz et al. | 71/86 |
| 4,352,689 | 10/1982 | Fritz et al. | 71/86 |
| 4,374,661 | 2/1983 | Fritz et al. | 71/86 |
| 4,401,454 | 8/1983 | Fritz et al. | 71/86 |
| 4,413,125 | 11/1983 | Gaertner | 71/86 |
| 4,557,751 | 12/1985 | Ronning et al. | 71/DIG. 1 |

FOREIGN PATENT DOCUMENTS

| | | | |
|---|---|---|---|
| 0122462 | 10/1976 | Fed. Rep. of Germany | 71/86 |
| 2022418 | 12/1979 | United Kingdom | 71/86 |

OTHER PUBLICATIONS

Kochmnn et al., "Agent for Stalk-Stabilizing Grains", CA 86, 1977, 184569x.

McCutcheon's Detergents and Emulsifiers, 1971 Annual, pp. 165, 210-212, 220, 221.

Levesque et al., "Foaming Regulation with Phosphates," Chem. Abs. 68:106278r (1968).

Encyclopedia of Chemical Technology, Kirk-Othmer, Third Ed., vol. 8, pp. 916-918 (1979).

S. Friberg, "Microemulsions and their Potentials," Chemtech, 1976, pp. 124-127.

*Primary Examiner*—Richard L. Raymond
*Attorney, Agent, or Firm*—Morgan & Finnegan

[57] ABSTRACT

Formulations containing aqueous phosphonic acid plant growth regulator dispersed in oil are disclosed that are stable and particularly suited for use with ultra-low volume spray apparatus.

16 Claims, No Drawings

PLANT GROWTH REGULATOR DISPERSIONS

FIELD OF INVENTION

This is a continuation of co-pending application Ser. No. 814,898, filed on Dec. 30, 1985, now abandoned.

This invention relates to dispersions of plant growth regulating compounds. More particularly it relates to water and oil formulations containing 2-haloethyl phosphonic acid compounds which are stable for extended periods of time over a wide range of ambient temperatures.

BACKGROUND OF THE INVENTION

The ability of 2-haloethyl phosphonic acid compounds to regulate plant growth is well known and is described for example in U.S. Pat. Nos. 3,879,188; 4,144,046, 4,240,819; 4,352,689: 4,374,661; and 4,401,454. These phosphonic acid plant growth regulators, when applied to plants, elicit a variety of different responses, such as increased yields, faster and more uniform ripening of fruit, induction of antilodging effects, breaking of apical dominance and the like, collectively referred to as ethylene or ethylene-type responses.

The preferred and most widely used phosphoric acid plant growth regulator compound is 2-chloroethylphosphonic acid which is known by the generic name "ethephon". Ethephon is normally stored in solution of relatively high concentration for reasons of convenience and to minimize degradation which begins to occur at pH levels above about pH 5. In concentrated form ethephon exhibits a pH of about 1.0. The concentrated solution is customarily diluted prior to application to plants at concentrations which exhibit a pH of about 3.5.

The most commonly used solutions of ethephon for plant treatment are aqueous solutions which are applied by conventional spray equipment. However, newer methods of application such as ultra-low volume (ULV) spray apparatus, work more effectively with non-aqueous solutions of the active chemical with oil based formulations being most preferred. Oil-based formulations of ethephon have the added advantage of better penetration of plant tissue than aqueous formulations.

A particular problem which it is sought to overcome by this invention is the rapid evaporation of water from aqueous formulations of ethephon which sometimes occurs when aqueous formulations of ethephon are applied through ULV apparatus. Such evaporation is so rapid that in some instances only the dry active reaches the plant.

The preparation of an oil-based formulation of such phosphonic acid plant growth regulators is therfore desirable both for improved plant tissue penetration and to permit application of these plant growth regulators with ULV apparatus. However, formulation of the phosphonic acid directly in an oil diluent is disfavored since the production of such formulations requires the use of essentially anhydrous phosphonic acid plant growth regulator. These strongly acidic phosphonic acid compounds are extremely hygroscopic and hence the anhydrous product is difficult and costly to prepare and difficult to maintain.

Formulations of aqueous solutions of agricultural chemicals in an oil base are known in the art. Prepartion of these emulsions or dispersions is accomplished by mixing the desired oil, water, active ingredient and an emulsifier in appropriate amounts to achieve the desired formulation. Such emulsion compositions are typically 30–80% by weight oil and 10–40% water. The emulsifier is present in smaller amounts, seldom exceeding 15% by weight of the final composition and more often at concentrations of 4–10%.

The preparation of chemically stable oil emulsions of the phosphonic acid growth regulators has proven difficult due to the low pH exhibited by these compounds. This low pH encourages the degradation of emulsifiers which rapidly erodes the stability of the emulsion and leads to phase separation. This severely limits the utility of these emulsions as spray formulations since phase separation of the spray formulation results in poor dispersion of phosphonic acid plant growth regulator in the target area.

Separation of formulation components may also cause the formation of solids which could clog the spray equipment. Acidic elements of the formulation, which are safe when dispersed in the oil carrier, can also cause rapid corrosion of spray equipment if the phases separate.

SUMMARY OF THE INVENTION

This invention provides dispersions containing 2-haloethyl phosphonic acid plant growth regulators that are stable and particularly well suited for use with ULV apparatus. They are prepared by mixing an aqueous solution of the 2-haloethyl phosphonic acid plant growth regulator with an oil and a substantial amount of surfactant. In some compositions a co-surfactant is also present.

It is a principal object of this invention to provide oil-based compositions that contain 2-haloethyl phosphonic acid plant growth regulating compounds, that are thermodynamically and chemically stable and that can be applied with ULV equipment.

It is a further object to prepare oil-based formulations of these compounds that are stable for periods on the order of at least two years at ambient temperatures (i.e., ranging from as low as about $-10°$ C. to as high as about 35° C.).

It is a further object to prepare oil-based dispersions of 2-haloethyl phosphonic acid plant growth regulators that can be easily cleansed from storage vessels and application equipment with a water rinse.

DETAILED DESCRIPTION OF THE INVENTION

This invention provides a stable plant growth regulating composition which comprises a dispersion, having a Brookfield viscosity of less than 800 cps and containing micelles no larger than about 300 nm, of:

(a) from about ten percent (10%) to about fifty percent (50%) by weight of a phosphonic acid plant growth regulator; and (b) from about twenty percent (20%) to about sixty percent (60) by weight of liquid which is substantially immiscible with water, which is not a solvent for said active compound, and which is stable at the pH of the active compound; and (c) from about five percent (5%) to about twenty-five percent (25) by weight water; and (d) from about ten percent (10%) to about forty percent (40) by weight hydrophobic surfactant or surfactant mixture which is stable at pH of said active compound.

The term phosphonic acid plant growth regulator, as used herein, includes not only 2-halothyl phosphonic acid compounds such as ethephon but also all derivatives thereof which act as plant growth regulators.

The phosphonic acid plant growth regulators suitable for use in this invention are described in U.S. Pat. Nos. 3,879,188; 4,374,661; 4,401,454; 4,240,819; and 4,352,689 which are incorporated herein by reference.

The preferred phosphonic acid plant growth regulator is 2-chloroethyl phosphonic acid, generically known by the generic name "ethephon". Ethephon is available as an aqueous concentrate of five to ninety-five percent. Preferred concentrates contain from about sixty to about eighty percent by weight of phosphonic acid plant growth regulator.

The terms: A "dispersion," "colloid" and "emulsion" as used herein describe macroscopically homoeneous but microscopically heteroeneous mixtures of two or more finely divided phases (i.e., solid, liquid or gas). The dispersions of this invention typically comprise liquid-liquid mixtures, one of the liquids being an aqueous solution of growth regulating compound, the other being an "oil", i.e., a liquid substantially immiscible with water. The term "liquid substantially immiscible with water" as used herein includes all liquids which, when mixed with water in the ratios described in this invention, will separate into two discrete phases after equilibration, absent agitation or presence of emulsifier.

Liquid-liquid dispersions consist of a first liquid, which forms the continuous phase in which micelles containing droplets of a second liquid, the discontinuous phase, are uniformly distributed. The term "micelle" refers to a molecular aggregate in which each surfactant molcule contains functional groups that interact independently with the oil and with the water. The functional group that interacts with the water is known as a hydrophile (i.e., water lover) or lipophobe (i.e., oil hater) while the group that bonds to the oil phase is designated a lipophile (i.e., oil lover) or hydrophobe (i.e., water hater). If water is the continuous phase and oil the secondary phase trapped in micelle centers, the dispersion is an oil-in-water (O/W) emulsion. In a water-in-oil (W/O) emulsion, also known as an "invert emulsion", the oil is the continuous phase and water the secondary phase. The micelles in such invert emulsions are "invert micelles"; the hydrophilic component of the surfactant surrounds the aqueous center while the hydrophobic component interacts with the surrounding oil.

The formulations of this invention are microemulsions which have a low viscosity, and are thermodynamically and chemically stable. The small micelle size, preferably ranging from about 10 to about 200 nm, produces a minimal amount of light scattering. Therefore most of the microemulsions of this invention are transparent, absent incorporation of a reagent or additive that is colored. In some instances the micelles of this formulation may be as large as about 300 nm in diameter, which may cause light scattering and render the formulations translucent.

The formulations of this invention must have sufficiently low viscosities to permit spraying onto target plants by conventional spray apparatus, and preferably by ULV equipment. A wide range of viscosities ar useful depending upon the apparatus used. Brookfield viscosities of greater than 800 cps are considred too thick for any conventional spray applicators and if the formulation is to be used in ULV equipment the viscosity preferably should not exceed about 300 cps and more preferably should be less than 100 cps. (The viscosities referred to are measured at 25° C. with a Brookfield Viscometer Model RVT using a number 4 spindle at 20 rpm.)

The concentration of phosphonic acid plant growth regulator compound used in the formulation of this invention preferably ranges from about ten percent (10) to about fifty percent (50) by weight, depending primarily upon the intended use of the formulation, particularly the plant to which it is applied and the specific plant growth response desired.

In the microemulsion formulations of this invention the continuous phase is an oil, i.e., liquid which is substantially immiscible with water, which is not a solvent for the active compounds employed, and which is stable at pH of the growth regulator. While some minor degree of intermixing may be tolerated, the oil and water must be sufficiently immiscible, in the ratio of water to oil used in a particular dispersion, that two discrete microscopic phases in the formulation will survive for extended periods of time over a temperature range of from about −20° C. to about +50° C. in the presence of all the ingredients incorporated into the formulation. Preferably, the dispersion should remain intermixed for at least two years in a temperature range of from −10° C. to +35° C. As a general rule, the oil should not be soluble more than 1% by weight in water. In addition, the selected oil must be stable in the acidic medium produced by the phosphonic acid comound, which may be as low as 0.5 pH. Compounds are not desirable for use as the oil in this invention which are sensitive to acid hydrolysis or protonation. These compounds include esters, amins and pyridinium compounds. Long-term stability of two years or more, especially at elevated temperatures, is difficult to achieve with such acid sensitive oils.

The oil employed should also be essentially non-phytotoxic to the target plants at the applied concentration. The oil should either be non-toxic or, if toxic, require a time to kill or injure the plant that exceeds the useful or remaining growing season of the plant. Further, if the formulation is to be used with ULV equipment, the oil is preferably sufficiently non-evaporative so that sprayed droplets of formulation reach the target plants in liquid form. The vapor pressure of the oil used for ULV applications must therefore be considered.

Representative of the oils useful in the formulations of this invention are aromatic hydrocarbons; extracts derived from natural sources; aliphatic hydrocarbons containing up to thirty carbon atoms, up to four non-adjacent double bonds, and up to four halogen, carboxyl or hydroxyl substituents (provided, of course, that the compound is a liquid immiscible with water). Mixtures of these oils can also be used. Especially preferred oils include mixtures of paraffins or isoparaffins; benzene or alkylbenzenes containing up to four $C_1$ to $C_4$ alkyl substituents; fatty acids containing from about twelve to about thirty carbon atoms, such as oleic acid and linoleic acid, and their triglyceride derivatives; and extracts derived from natural sources, e.g., tall oil, palm oil, cottonseed oil, linseed oil, soybean oil, peanut oil, castor oil and lanolin. These listings are merely illustrative. Any oil having the required physical properties can be used.

The amount of oil in a particular formulation is dependent upon a number of empirical characteristics of the ingredients in that formulation. The oil is present in an amount relative to the amount of water such that the oil forms the continuous phase in the final formulation. Usually the oil should be present in an amount by weight that exceeds the amount of water. As a general rule, weight percentages of from about twenty to about sixty percent of oil are useful.

In general, the water should not exceed twenty percent by weight, although in some instances, higher values can be useful. For example, in a composition containing a small amount (about 10%) growth regulator and a high amount of surfactant (about 30%) and a substantial amount of oil (about 35), approximately 25% by weight water is required. Usually, however, the amount of water will seldom exceed 15% by weight of the final formulation.

As with the oil, the hydrophobic surfactant must be chemically stable at the low pH conditions produced by the phosphonic acid plant growth regulator compound, especially the very low pH conditions produced by the preferred concentrated aqueous solutions of phosphonic acid plant growth regulators. Further, the surfactant must not raise the pH to a level that would lead to decomposition of the active compound. As a general rule any hydrophobic anionic, cationic or nonionic surfactant that does not raise the system pH can be used. Formulations using anionic or nonionic surfactants appear to offer better long term stability.

Care must be taken in selecting the surfactant since some ester-containing surfactants may undergo slow hydrolysis, leading to gradual deterioration of the formulation if it is stored at elevated temperatures for extended periods of time. Further, many cationic surfactants contain nitrogenous functional groups, which, over a period of time, may lead to decomposition of the preferred phosphonic acid compounds.

The extent of interaction between water, oil and surfactant can be predicted from the hydrophilic-lipophilic balance (HLB) of the surfactant. The HLB values for most surfactants are reported on a scale of 0–20 in which values of 0 to 6 indicate strong hydrophobicity (or lipophilicity), 6 to 10 moderate hydrophobicity, 10 to 14 moderate hydrophilicity (or lipophobicity) and 14 to 20 strong hydrophilicity.

The requirement that the surfactant be hydrophobic arises because of the nature of the oils that are most useful in the compositions of this invention. The substituted and unsubstituted aliphatic and aromatic hydrocarbons and the extracts from natural sources are nonpolar or only slihtly polar materials. As a general rule preparation of water-in-oil dispersions of these kinds of liquids requires a hyrophilic surfactant of high HLB, i.e., approximately 14–17. It was discovered, however, that in the presence of ten to fifty percent 2-haloethyl phosphonic acid, such surfactants fail to produce stable microemulsions. The difficulty can be overcome if a hydrophobic surfactant, i.e., a surfactant of HLB less than about 8, is used.

Without intending to be bound by any theory proposed, it is thought that the tendency of the phosphonic acids in water to hydrogen bond with the surfactant accounts for this surprising observation. As the acid interacts with the water and the surfactant, the resulting aggregate of surfactant and acid apparently has an effective HLB value of 13 or more. When a surfactant with a high HLB value is utilized either alone, or as the major component in combinations of surfactants, the effective HLB is raised to such a high value that no microemulsion forms at all, or one is formed but its thermodynamic stability is short-lived. Whatever the mechanism of surfactant-acid interaction may be, it is clear that the preparation and stability of emulsions of 2-haloethyl phosphonic acid require the use of hydrophobic surfactants when the oil of choice has the properties of those listed above.

Representative of the surfactants that can be used in the compositions of this invention are mono-substituted glycerol derivatives of fatty acids containing from about ten to about thirty carbon atoms, e.g., monostearates, monooleates and monolaurates; sugar-based fatty acid derivatives containing from about ten to about thirty carbon atoms in the fatty acid chain; acetylated glycerides of natural oils (i.e., liquids extracted from natural sources); and polyethoxylated alcohols or alkylphenols with branched or straight chain alkyl groups containing from about six to about thirty carbon atoms. Ester, phosphate ester and phosphate acid analogues of many of these agents may also be useful. Stable hydrophobic amine or amide derivatives may also prove effective.

The especially preferred surfactants are the anionic or nonionic polyethoxylated derivatives of alcohols and phenols containing from about eight to about thirty carbon atoms and less than twenty moles of ethylene oxide per mole of alcohol or phenol.

To achieve maximum dispersion and stability, the compositions of this invention require the use of substantial amounts of surfactant. While the optimum amount must be determined empirically according to the amount of growth regulator and the nature and amount of the oil to be used, weight percentages ranging from about ten to about forty percent are typical.

One very unexpected property of some of the microemulsions of this invention is their toleration of changes in the formulation HLB. Formation of a stable dispersion usually requires a delicate balancing of oil, water and surfactant. This is particularly true for microemulsions. For example, if a highly polar liquid or a very hydrophilic surfactant (i.e., one having an HLB value of 17 or more) were added to a stable microemulsion of non-polar oil, water and surfactant, the dispersion would separate into phases, either immediately or after standing, because the thermodynamic balance had been destroyed. However, microemulsions containing 2-haloethyl phosphonic acid and a hydrophobic surfactant tolerate the addition of significant quantities of very hydrophilic anionic or nonionic surfactant without losing their thermodynamic stability. An emulsion containing as little as ten to fifteen percent by weight hydrophobic surfactant will remain stable if as much as nine percent by weight very hydrophilic surfactant is added. This characteristic is of practical advantage in that apparatus used to apply the emulsion can be cleaned simply with water.

In the absence of the hydrophilic surfactant, emulsion rsidues resist water because the surfactant is so hydrophobic that when rinse water is introduced into the apparatus, the emulsion residue coalesces and the water-immiscible liquid adheres to the walls of the apparatus. Incorporation of hydrophilic surfactant into the emulsion permits the emulsion residue to mix with the water and be washed away.

To prepare the compositions of this invention, the components can be added in any order but must be mixed together with sufficient vigor until the microemulsion forms, usually at ambient temperatures. Occasionally slight heating up to about 50° C. may be required. If, however, the proper amounts of growth regulator, oil, water or surfactant are unknown, or if the particular ingredients interact so that no microemulsion forms after mixing, a co-surfactant may be added.

A "co-surfactant" is a low molecular weight non-ionizing oranic compound which contains a polar functional group and which enhances the interaction of surfactant, water and oil. The co-surfactant can be incorporated into the mixture at any time during the preparation. If, however, the proportions of oil to water in a particular formulation must be very delicately balanced, addition of the co-surfactant should be done after the growth regulator, water, surfactant and oil have been mixed into a macroemulsion. The macroemulsion should then be viorously mixed while co-surfactant is titrated into it. Titration continues until the opaque macroemulsion becomes transparent or translucent. Should the macroemulsion be colored, then some indication for conversion of macroemulsion to microemulsion should be monitored; for example, there might be a color change or disappearance of cloudiness.

Traditional co-surfactants are straight chain aliphatic alcohols containing from one to aout six carbon atoms. For purposes of this invention branched or straight chain $C_1-C_{15}$ mono or polyhydroxy alcohols are suitable; formulations containing t-butanol, $C_8-C_{10}$ linear alcohols, ethylene glycol or propylene glycol have given especially stable microemulsions. Urea and substituted ureas containing up to four $C_1-C_3$ alkyl substituents, and dialkylformamides containing $C_1-C_3$ alkyl groups are useful; urea and dimethylformamide have proved particularly beneficial. Trialkylphosphates containing $C_1-C_6$ straight or branched alkyl groups can be used; tributylphosphate is an effective co-surfactant.

As with the other ingredients, the amount of co-surfactant for a particular formulation must be determined empirically. However, typical concentrations range from about five to about thirty percent. When a co-surfactant is used, the amount of surfactant required in a formulation is generally reduced by about five to ten percent relative to formulations with no co-surfactant.

The toleration of the microemulsion to changes in system HLB is generally not destroyed by the use of a co-surfactant. We have discovered, however, that surfactants with slightly higher HLB values, approximately eight to nine, can be used if the formulation contains a co-surfactant.

The following examples are set forth for purposes of illustration.

A. FORMULATIONS WITHOUT CO-SURFACTANT

EXAMPLE 1

A microemulsion was prepared by combining 3.6 g 70% aqueous 2-chloroethyl phosphonic acid, 3.6 g mixture of aromatic hydrocarbons (Aromatic 150, Exxon), and 2 g nonionic ethoxlated linear alcohol surfactant (Alfonic 1412-40, Conoco) and blending until a transparent liquid formed. The microemulsion was stable, chemically and thermodynamically, up to 50° C.

EXAMPLE 2

A microemulsion was prepared by combining 3 g mixture of isoparaffinic hydrocarbons (Isopar M, Exxon), 3.5 g nonionic ethoxylated linear alcohol surfactant (Alfonic 1412-40, Conoco) and 3.5 g 70% aqueous 2-chloroethyl phosphonic acid and blending until a transparent liquid formed. The microemulsion was stable, chemically and thermodynamically, up to 50° C.

EXAMPLE 3

A microemulsion was prepared by combining 3 g mixture of aromatic hydrocarbons (HAN, Exxon), 3 g nonionic ethoxylated linear alcohol surfactant (Alfonic 1412-40, Conoco) and 2 g 70% aqueous 2-chloroethyl phosphonic acid and blending until a transparent liquid formed. The microemulsion was stable, chemically and thermodynamically, up to 50° C.

EXAMPLE 4

A microemulsion was prepared by combining 5.3 g mixture of isoparaffinic hydrocarbons (Isopar M, Exxon), 2.8 g nonionic ethoxylated linear alcohol surfactant (Alfonic 1412-40, Conoco) and 1.9 g 70% aqueous 2-chloroethyl phosphonic acid and blending until a transparent liquid formed. The microemulsion was stable, chemically and thermodynamically, up to 50° C.

B. FORMULATIONS WITH CO-SURFACTANT

EXAMPLE 5

A microemulsion was prepared by adding to 30 g tall oil (L5 grade, Westvaco), 10 g free acid of a complex organic phosphate ester anionic surfactant (Gafac RM-510, GAF) and 10 g linear $C_9-C_{11}$ alcohol mixture (Neodol 91, Shell), mixing until dissolution was complete, stirring in 30 g 70% aqueous 2-chloroethyl phosphonic acid and adding this macroemulsion to an equal volume of water. The microemulsion showed poor stability, separating into two phases after several hours.

EXAMPLE 6

A microemulsion was prepared by combining 0.7 g urea, 4 g 70% aqueous solution of 2-chloroethyl phosphonic acid, 1 g organic phosphate ester anionic surfactant (Emphos CS-341, Witco) and 4 g tall oil (L5 grade, Westvaco) and shaking until a clear liquid formed. The microemulsion was stable, chemically and thermodynamically, from −20° C. to 50° C.

EXAMPLE 7

A micromulsion was prepared by combining 4 g tall oil (L5 grade, Westvaco), 1 g organic phosphate ester anionic surfactant (Emphos CS-341, Witco), 0.5 g ethoxylated nonylphenol nonionic surfactant (Teritol NP-6, Union Carbide), 1.2 g propylene glycol and 4 g 70% aqueous 2-chloroethyl phosphonic acid and stirring until a clear liquid formed. The microemulsion was stable, chemically and thermodynamically, up to 50° C.

EXAMPLE 8

A microemulsion was prepared by combining 5 g oleic acid, 2 g free acid of complex organic phosphate anionic surfactant (Gafac PE-510, GAF), 1 g urea and 5 g 70% aqueous 2-chloroethyl phosphonic acid and mixing until a clear liquid formed. The microemulsion was stable, chemically and thermodynamically, up to 50° C.

EXAMPLE 9

A microemulsion was prepared by combining 4 g tall oil (L5 special grade, Westvaco), 1 g orqanic phosphate ester anionic surfactant (Emphos CS-341, Witco), 1 g tributylphosphate and 6 g 70% aqueous 2-chloroethyl phosphonic acid and mixing until a transparent liquid formed. The microemulsion was stable, chemically and thermodynamically, up to 50° C.

EXAMPLE 10

A microemulsion was prepared by combining 4 g tall oil (L5A special grade, Westvaco), 1 g organic phosphate ester anionic surfactant (Emphos CS-341, Witco), 1 g t-butanol and 6 g 70% aqueous 2-chloroethyl phosphonic acid and mixing until a transparent liquid formed. The microemulsion was stable, chemically and thermodynamically, up to 50° C.

C. FORMULATIONS WITH ADDED HYDROPHILIC SURFACTANT

EXAMPLE 11

A microemulsion was prepared by combining 4.5 g mixture of aromatic hydrocarbons (Aromatic 150, Exxon), 1.1 g free acid of complex oranic phosphate ester anionic (hydrophobic) surfactant (Gafac RM-410, GAF), 0.8 g polyethoxylated nonylphenol (hyrophilic) surfactant (Arnox 950, Arjay) and 2.5 g 70% aqueous 2-chloroethyl phosphonic acid and mixing until a transparent liquid formed. The microemulsion was stable, chemically and thermodynamically, up to 50° C. Residues remaining in storage or application apparatus were easily washed away with a water rinse.

EXAMPLE 12

A microemulsion was prepared by combining 2.5 g tridecyloxypoly (ethyleneoxy) ethanol nonionic (hydrophobic) surfactant (Emulphogene BC-420, GAF), 1.8 g nonylphenoxypoly (ethyleneoxy) ethanol nonionic (hydrophilic) surfactant (Igepal C0-997, GAF), 0.5 g ethlene glycol, 3.4 g mixture of isoparaffinic hydrocarbons (Isopar M, Exxon) and 1.8 g 70% aqueous 2-chloroethyl phosphonic acid and mixing until a transparent liquid formed. The microemulsion was stable, chemically and thermodynamically, up to 50° C. Residues remaining in storage or application apparatus were easily washed away with a water rinse.

EXAMPLE 13

A microemulsion was prepared by combining 2.5 g nonionic ethoxylated linear alcohol surfactant (Alfonic 1412-40, Conoco), 1 g methyl isoamyl ketone, 3 g 70% aqueous solution of 2-chloroethyl phosphonic acid and 3 g mixture of isoparaffinic hydrocarbons (Isopar M, Exxon) and mixing until a transparent liquid formed. The microemulsion was stable chemically and thermodynamically, up to 50° C. Residues remaining in storage or application apparatus were easily washed away with a water rinse.

EXAMPLE 14

A microemulsion was prepared by combining 2.5 g tridecyloxypoly (ethyleneoxy) ethanol nonionic (hydrophobic) surfactant (Emulphogene BC-420, GAF), 1.5 g nonylphenoxypoly (ethyleneoxy) ethanol nonionic (hydrophilic) surfactant (Igepal CO-997, GAF) 0.5 g methyl isoamyl ketone, 2.5 g mixture of isoparaffinic hydrocarbons (Isopar M, Exxon) and 3 g 70% aqueous solution of 2-chloroethyl phosphonic acid and mixing until a transparent liquid formed. The microemulsion was stable, chemically and thrmodynamically up to 50° C. Residues were easily washed from storage and application equipment with a water rinse.

The compositions of this invention can be applied with ULV equipment in neat form or after dilution with an oil extracted from a natural source; cottonseed or soybean oil are very commonly used for this purpose. The decision to dilute will depend upon the concentration of active in the microemulsion, the ease of applying the formulation in neat form and the concentration of active needed to induce the desired response in the plant. Coverages ranging from about 0.1 to as high as about 30 lbs a.i./A have been used, although the emulsions are customarily applied at rates ranging from 0.5 to 2 lb a.i./A.

The following examples are given to illustrate the utility of these compositions in regulating growth in cotton plants. In these examples $T_0$ is the day of application, $T_1$ is observation seven days later, and $T_2$ is observation fourteen days later.

EXAMPLE A

The formulation of example 2 was applied with ULV equipment by airplane under a clear sky with no wind at a temperature of 82° F. to twenty rows of a field planted four and one half months earlier with Stoneville 825 cotton. Coverage of 2-chloroethyl phosphonic acid was 1 lb. a.i./A. Interior parts of the treated plot were monitored for % boll opening, density of green bolls and % defoliation over a two week period. Observations were compared to those obtained for six untreated rows and to a field on which an aqueous solution of 2-chloroethyl phosphonic acid was applied at 1 lb. a.i./A by conventional spray equipment. Results are summarized in Table I.

EXAMPLE B

The formulation of example 4 was applied with ULV equipment by airplane under a clear sky with no wind at a temperature of 82° F. to twenty rows of a field planted four and one half months earlier with Stoneville 825 cotton. Coverage of 2-chloroethyl phosphonic acid was 0.5 lb. a.i./A. Interior parts of the treated plot were monitored for % boll opening, density of green bolls and % defoliation over a two week period. Observations were compared to those obtained for six untreated rows and to a field on which an aqueous solution of 2-chloroethyl phosphonic acid was applied at 1 lb a.i./A by conventional spray equipment. Results are summarized in Table I.

TABLE I

| Example | Boll Opening (%) | | | No. Green Bolls/ 10 ft. row | | | Defoliation (%) | | |
|---|---|---|---|---|---|---|---|---|---|
| | $T_0$ | $T_1$ | $T_2$ | $T_0$ | $T_1$ | $T_2$ | $T_0$ | $T_1$ | $T_2$ |
| A | 72 | 98 | 100 | 39 | 3 | 0 | 40 | 99 | 98 |
| Aq. ref. *A | 52 | 70 | 99 | 75 | 33 | 5 | 31 | 83 | 90 |
| B | 60 | 97 | 100 | 45 | 3 | 1 | 55 | 96 | 96 |
| Aq. ref. *B | 69 | 73 | 96 | 48 | 22 | 5 | 31 | 83 | 89 |
| UTC** | 65 | — | 75 | — | — | — | — | — | 35*** |

*Aq. ref. = aqueous reference solution applied at the same coverage as the relevant example
**UTC = untreated controls
***some regrowth was observed When aqueous solutions of 2-chloroethyl phosphonic acid are applied to cotton fields under similar conditions at identical coverages, the effects on boll opening, formation and defoliation are comparable, to, and perhaps slightly poorer than, those reported above with the microemulsions of Examples 2 and 4. It is clear that the compositions of this invention are at least equally effective as known aqueous growth regulator formulations.

They offer the added advantage of being applicable with the modern ULV equipment.

The results of Examples A and B are shown on Table I. Not that the microemulsion of Examples 2 and 4 produced enhanced results when compared with aqueous solution applied at the same rate. The microemulsion compositions of the invention outperformed the aqueous solutions based on observations two weeks after application. Moreover, the inventive formulations induced comparable if not better results in just seven days than the aqueous solutions produced after fourteen days.

What is claimed is:

1. A stable plant growth regulating composition which comprises a dispersion, having a Brookfield viscosity of less than 800 cps, said dispersion being a microemulsion, and containing micelles no larger than 300 nm in diameter, of:
   a. from about ten percent (10%) to about fifty percent (50%) by weight of 2-chloroethylphosphonic acid; and
   b. from about twenty percent (20%) to about sixty percent (60%) by weight of a hydrocarbon oil which is:
      i. substantially immiscible with water;
      ii. stable at the pH of said regulator compound, said pH being as low as 0.5 pH; and
      iii. said hydrocarbon oil forming a continuous phase of said microemulsion; and
   c. from about five percent (5%) to about twenty-five percent (25%) by weight water; and
   d. from about ten percent (10%) to about forty percent (40%) by weight of hydrophobic surfactant selected from the group consisting of phosphate acid, phosphate esters, or one or more anionic or nonionic polyethoxylated alcohol or phenol compounds containing from about eight to about twenty carbon atoms in the alkyl chain and less than twenty moles of ethylene oxide per mole of alcohol or phenol, said surfactant having an HLB less than about 8, or surfactant mixture which is stable at said pH of said regulator compound.

2. A composition according to claim 1 wherein said Brookfield viscosity is less than 300 cps.

3. A composition according to claim 2 wherein said hydrocarbon oil is:
   a. an aromatic hydrocarbon;
   b. an organic extract derived from a natural source; or
   c. an aliphatic hydrocarbon containing up to thirty carbon atoms, up to four non-adjacent double bonds, and up to four halogen, carboxyl or hydroxyl substituents; or
   d. a mixture thereof.

4. A composition according to claim 3 wherein said hydrocarbon oil is a paraffin, isoparaffin, benzene, alkylbenzene containing up to four $C_1$ to $C_4$ substituents, a fatty acid or triglyceride derivative containing from about twelve to about thirty carbon atoms, tall oil, palm oil, cottonseed oil, linseed oil, soybean oil, peanut oil, castor oil, lanolin or a mixture thereof.

5. A composition according to claim 3 and further comprising from about five percent (5%) to about thirty percent (30) by weight of co-surfactant.

6. A composition according to claim 5 wherein said co-surfactant is a branched or straight chain $C_1$–$C_{15}$ mono or polyhydroxy alcohol; urea or substituted urea containing up to four $C_1$–$C_3$ alkyl substituents; a dialkylformamide containing $C_1$–$C_3$ alkyl groups or a trialkylphosphate containing $C_1$–$C_6$ straight or branched alkyl groups.

7. A composition according to claim 6 wherein said co-surfactant is t-butanol; a mixture of $C_8$–$C_{10}$ alcohols; dimethylformamide; ethylene glycol; propylene glycol; or tributyl phosphate.

8. A composition according to claim 5 which also includes up to ten percent (10%) by weight of hydrophilic surfactant of HLB value at least 16.

9. A composition which comprises from about twenty prcent (20%) to about thirty percent (30%) by weight 2-chloroethyl phosphonic acid, from about seven percent (7%) to about fourteen percent (14%) by weight water, from about thirty-five percent (35%) to about forty percent (40%) by weight mixture of aromatic hydrocarbons and from about twenty percent (20%) to about twenty-five percent (25%) by weight nonionic ethoxylated linear alcohol.

10. A composition which comprises from about ten percent (10%) to about twenty-five percent (25%) by weight 2-chloroethyl phosphonic acid, from about five percent (5%) to about ten percent (10%) by weight water, from about thirty percent (30%) to about thirty-five percent (35%) by weight mixture of isoparaffins and from about twenty-five percent (25%) to about thirty-five percent (35%) by weight nonionic ethoxylated linear alcohol.

11. A composition which comprises from about fiften percent (15%) to about twenty-five percent (25%) by weight 2-chloroethyl phosphonic acid, from about seven percent (7%) to about ten percent (10%) by weight water, from about fifty percent (50%) to about fifty-five percent (55%) by weight mixture of aromatic hydrocarbons, from about ten percent (10%) to about fourteen percent (14%) by weight hydrophobic anionic free acid of complex organic phosphate ester and from about eight percent (8%) to about ten percent (10%) by weight hydrophilic polyethoxylated nonylphenol.

12. A method for regulating plant growth by achieving ethylene or ethylene-type responses of increasing yields, increasing speed of fruit ripening, inducing antilodging effects, breaking of apical dominance or a combination of these responses which comprises applying to the plant an effective amount of the plant growth regulator composition of claim 1.

13. A composition according to claim 3 wherein the amount of said water of said dispersion ranges from about five percent (5%) to fifteen percent (15%) by weight.

14. A composition according to claim 13 wherein said micelles range from about 10 to about 200 nm in diameter.

15. A composition according to claim 14 wherein said Brookfield viscosity is less than about 100 cps.

16. The composition of claim 1 wherein the surfactant is a phosphate ester or phosphate acid.

* * * * *